(12) United States Patent
Leberthon

(10) Patent No.: US 10,869,959 B2
(45) Date of Patent: Dec. 22, 2020

(54) METHOD AND DEVICE FOR TREATING CANCER

(71) Applicant: Brian J. Leberthon, Arcadia, CA (US)

(72) Inventor: Brian J. Leberthon, Arcadia, CA (US)

( * ) Notice: Subject to any disclaimer, the term of this patent is extended or adjusted under 35 U.S.C. 154(b) by 818 days.

(21) Appl. No.: 15/600,384

(22) Filed: May 19, 2017

(65) Prior Publication Data

US 2018/0001013 A1    Jan. 4, 2018

Related U.S. Application Data

(62) Division of application No. 14/879,019, filed on Oct. 8, 2015, now Pat. No. 9,656,014, which is a division of application No. 13/830,276, filed on Mar. 14, 2013, now Pat. No. 9,227,005.

(51) Int. Cl.
*A61M 1/34* (2006.01)
*A61M 1/36* (2006.01)

(52) U.S. Cl.
CPC ........ *A61M 1/3486* (2014.02); *A61M 1/3489* (2014.02); *A61M 1/3493* (2014.02); *A61M 1/362* (2014.02); *A61M 1/3616* (2014.02); *A61M 1/3687* (2013.01)

(58) Field of Classification Search
CPC ...... A61M 1/36; A61M 1/362; A61M 1/3687; A61M 1/3621
See application file for complete search history.

(56) References Cited

U.S. PATENT DOCUMENTS

| | | | |
|---|---|---|---|
| 3,864,259 A | * | 2/1975 | Newhart ............. A61M 1/1696 604/6.06 |
| 4,289,623 A | * | 9/1981 | Lee ........................ B01D 63/02 210/247 |
| 4,350,156 A | | 9/1982 | Malchesky et al. |

(Continued)

FOREIGN PATENT DOCUMENTS

| | | |
|---|---|---|
| EP | 14775499 | 11/2016 |
| WO | WO 2011/044329 A2 | 4/2011 |

(Continued)

OTHER PUBLICATIONS

Eneman et al. (Cancer Management in Patients With End-Stage Renal Disease, Aug. 1, 2005, https://www.cancernetwork.com/view/cancer-management-patients-end-stage-renal-disease, accessed Jul. 6, 2020) (Year: 2005).*

*Primary Examiner* — Ariana Zimbouski
(74) *Attorney, Agent, or Firm* — John J. Connors; Connors & Assoc. PC

(57) ABSTRACT

A method and device treats cancer where blood from a cancer patient passes through an array of passageways within an interior of a chamber. The passageways include wells having porous membrane wall portions that enable a molecular-sized activating agent in a carrier fluid that enhances an immune response to pass through these porous wall portions. Pore size is such to allow the molecular-sized activating agent in the interior of the chamber to enter the wells yet prevents immune cells and cancer cells in the wells to pass through the porous wall portions into the interior of the chamber. Blood is retained in the wells so that it remains in contact with the immune cells and cancer cells for a predetermined period sufficient to enhance an immune response. Then the cells with an enhanced immune response are return to the patient.

2 Claims, 2 Drawing Sheets

(56) References Cited

U.S. PATENT DOCUMENTS

| | | |
|---|---|---|
| 4,605,394 A | 8/1986 | Skurkovich |
| 4,612,007 A | 9/1986 | Edelson |
| 4,844,893 A | 7/1989 | Honsik et al. |
| 4,955,857 A | 9/1990 | Shettigar |
| 5,209,717 A | 5/1993 | Schmoll et al. |
| 5,628,727 A | 5/1997 | Hakkey et al. |
| 5,649,904 A | 7/1997 | Gianni |
| 5,676,644 A | 10/1997 | Toavs et al. |
| 5,874,308 A | 2/1999 | Kilburn et al. |
| 6,528,057 B1 | 3/2003 | Ambrus et al. |
| 6,855,291 B2 | 2/2005 | Patterson et al. |
| 7,094,378 B1 | 8/2006 | Goodrich, Jr. et al. |
| 7,744,883 B2 | 6/2010 | Bristow |
| 7,763,243 B2 | 7/2010 | Lum et al. |
| 2002/0071825 A1 | 6/2002 | Schall et al. |
| 2003/0147812 A1 | 8/2003 | Ueberle |
| 2006/0091056 A1 | 5/2006 | Bruggar |
| 2009/0047288 A1 | 2/2009 | Yan |
| 2010/0130904 A1 | 5/2010 | Kirber |
| 2012/0201799 A1 | 8/2012 | Federspiel et al. |
| 2013/0338102 A1* | 12/2013 | Martis ............... A61P 31/04 514/54 |
| 2014/0030238 A1 | 1/2014 | Perritt et al. |
| 2015/0076053 A1* | 3/2015 | Higgitt ............ A61M 1/1641 210/321.71 |

FOREIGN PATENT DOCUMENTS

| WO | WO 2011/163533 A2 | 12/2011 |
|---|---|---|
| WO | PCT/US2014/021430 | 7/2014 |

\* cited by examiner

METHOD AND DEVICE FOR TREATING CANCER

RELATED APPLICATIONS AND INCORPORATION BY REFERENCE

This utility application is a continuation application of U.S. application Ser. No. 14/879,019, entitled "METHOD AND DEVICE FOR TREATING CANCER," filed Oct. 8, 2015, now U.S. Pat. No. 9,656,014, which is a national phase application of International Application No. PCT/US14/21430, entitled "METHOD AND DEVICE FOR TREATING CANCER," filed Mar. 6, 2014, which claims the benefit under 35 USC § 120 of U.S. patent application Ser. No. 13/830,276, entitled "METHOD AND DEVICE FOR TREATING CANCER," filed Mar. 14, 2013, now U.S. Pat. No. 9,227,055. All of these related applications are incorporated herein by reference and made a part of this application. Moreover, any and all U.S. patents, U.S. patent applications, and other documents, hard copy or electronic, cited or referred to in this application are incorporated herein by reference and made a part of this application.

DEFINITIONS

The words "activating agent" means a substance that enhances directly or indirectly the immune response of immune cells.

The word "antibody" or word "antibodies" is a protein or proteins that bind specifically to a particular antigen, and often has immune function.

The word "antigen" is a substance that is bound by antibodies and, under the correct circumstances, can prompt the generation of antibodies and cause an immune response. All molecular structures that can be specifically bound by antibodies are antigens whether or not the interaction between antigen and antibody leads to subsequent responses by the immune system. Immunogenicity and antigenicity are related, but distinct. Immunogenicity is the ability to induce a humoral and/or cell-mediated immune response. Antigenicity is the ability to combine specifically with the final products of the [immune response] (i.e. secreted antibodies and/or surface receptors on T-cells or other effector cells). Although all molecules that have the property of immunogenicity also have the property of antigenicity, the reverse is not true.

The word "chemotaxin(s) means a substance that induces chemotaxis.

The word "chemotaxis" means a phenomenon whereby eukaryotic cells, bacteria, and single-cell organisms direct their movements according to certain chemicals in their environment. Positive chemotaxis occurs if the movement is toward a higher concentration of the chemical in question. Conversely, negative chemotaxis occurs if the movement is in the opposite direction.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The word "cytokine(s)" means small cell-signaling protein molecules that are secreted by numerous cells and are a category of signaling molecules used extensively in intercellular communication. Cytokines can be classified as proteins, peptides, or glycoproteins; the term "cytokine" encompasses a large and diverse family of regulators produced throughout the body by cells of diverse embryological origin.

The words dendritic cell(s) are cells that are associated with antigen presentation. Antigen presentation is the process wherein an antigenic molecule is consumed by a cell, usually by phagocytosis, broken down within the cell, and components of the antigenic molecule are subsequently displayed on the surface of the dendritic cell along with other molecular signals to stimulate and specifically sensitize other cells of the immune system to engender an immune response. These cells may be effector cells or cells capable of directing other cells of the immune system.

The words "effector cell(s)" are cells of the immune system which are responsible for enacting directly or indirectly the ultimate operation of immunity, such as, for example, lysis of tumor cells or phagocytosing (ingesting) targets (cells or other materials) associated with antigens. These cells may include T-cells, NK cells, macrophages, monocytes and granulocytes.

The words "ex vivo" mean taking place in a chamber apart from the patient but while the chamber is connected to a patient's body so blood from the patient flows into the chamber and is returned to the patient without disconnection.

The words "in vitro" mean taking place in a test tube or other vessel apart from the patient and not connected to a patient's body.

The words "in line" mean within a chamber outside a patient's body that is connected to the patient to draw blood into the chamber.

The word "lymphokine(s)" means a substance that produces an immune system response, for example, a subset of cytokines produced by a type of immune cell known as a lymphocyte. They are protein mediators typically produced by T cells to direct the immune system response by signaling between its cells. Lymphokines have many roles, including the attraction of other immune cells, including macrophages and other lymphocytes, to an infected site and their subsequent activation to prepare them to mount an immune response. Circulating lymphocytes can detect a very small concentration of lymphokine and then move up the concentration gradient towards where the immune response is required. Lymphokines also aid B cells to produce antibodies. Important lymphokines secreted by the T helper cell include: Interleukin 2, Interleukin 3, Interleukin 4, Interleukin 5, Interleukin 6, Granulocyte-macrophage colony-stimulating factor, and Interferon-gamma.

The words "substantially" and "essentially" have equivalent meanings.

BACKGROUND

Cancer in its many forms is uncontrolled growth of abnormal cells in the body. There are immune cells in a patient's blood, which, in general, are white blood cells (WBC) including, for example, dendritic cells, antigen presenting cells (APC's), and effector cells. Enhancing the growth or effectiveness of immune cells in a patient being treated for cancer is highly desirable.

Cancerous cells are frequently referred to as malignant cells and often form tumors. Symptoms of cancer depend on the type and location of the tumor. Various anti-cancer substances having the potential to suppress the cancer's growth or destroy cancer cells are injected into a cancer patient. For example, biotech companies have developed antibodies that attach to effector cells or other targets within a patient's blood or areas accessible to the blood stream that may result in the regression of the cancer, or at least suppression of its growth. These antibodies may act by different mechanisms, such as by attaching to growth factors, or their receptors, and interfering with growth signals. Such mechanisms may also operate by prohibiting new blood vessel growth into the tumor. Other antibodies attach to various antigens on tumor cells, and are believed to operate by allowing effector cells to localize to the tumor cells and destroy them.

Attachment of antibodies to effector cells, however, does not always lead to immediate and complete termination of the cancerous growth or provoke an immune response from the patient. Nevertheless, such attachment is desirable because anti-tumor activity on the part of effector cells is conducted by such attachment of the antibodies. Other anti-cancer substances beside antibodies may interact with a patient's effector cells to provoke an immune response, whether or not any specific antibody attachment occurs. An example of this is interferon, which is known to stimulate effector cells against cancer. Immune responses may be different with different types of cancers, and conceivably in the same tumor type in different patients. Provoking an immune response is a way to enable the patient's own immune system to suppress the growth of the cancer.

SUMMARY

My method, using my device, is designed to provoke an immune response in a patient. My method and device have one or more of the features depicted in the embodiments discussed in the section entitled "DETAILED DESCRIPTION OF ONE ILLUSTRATIVE EMBODIMENT." The claims that follow define my method and device, distinguishing them from the prior art; however, without limiting the scope of my method and device as expressed by these claims, in general terms, some, but not necessarily all, of their features are:

One, in my method a patient's blood is introduced into wells in walls of passageways through which the blood flows and an activating agent is introduced into the wells through a porous membrane portion in the wells. The patient's blood is retained in the wells for a predetermined period sufficient for the activating agent to enhance an immune response of the patient's immune cells in the blood flowing into the wells. Typically, the blood is pumped through the passageways and a carrier fluid including the activating agent is pumped through an interior of a chamber holding the passageways. The blood flow through the passageways may be countercurrent to the flow of carrier fluid through the interior of the chamber. Different activating agents may be periodically introduced into the fluid. For example, one of the different activating agents may be a chemotaxin and the other different activating agent may be a cytokine.

Two, my device includes the chamber with an inlet and an outlet in fluid communication with an interior of the chamber to enable the fluid containing the activating agent to flow in one direction into the inlet, through the interior of the chamber, and out the outlet. There are a plurality of tubular passageways within the chamber that may have a diameter substantially from 50 to 500 microns. The passageways are assembled and configured to be placed in fluid communication with a patient to enable blood from the patient to flow through the passageways in a direction opposite to the direction of the fluid flow.

Three, the tubular passageways have an interior wall with a plurality of wells Four, therein having open mouths of predetermined dimensions that enable immune cells and cancer cells in a patient's blood flowing through the passageways to pass through the open mouths and enter the wells. The width of the open mouth of a well may be substantially from 20 to 200 microns, and the depth of a well may be substantially from 20 to 100 microns. The porous membrane portion has a predetermined pore size that enables the activating agent in the fluid flowing through the interior of the chamber to pass through a well's porous membrane and enter the well yet prevents immune cells and cancer cells in a well to flow through the membrane into the interior of the chamber. The pores is sufficiently large in size to enable chemotaxins and cytokines to pass through the membrane, yet sufficiently small in size to prevent immune cells and cancer cells in the blood to pass through the porous membrane portions into the interior of the chamber.

Four, the patient's blood is circulated through the passageways for a predetermined period sufficient to enhance an immune response in the immune cells held within the wells and then the connection between the patient and the device is terminated after returning to the patient the cells with the enhanced immune response.

DESCRIPTION OF THE DRAWING

The one embodiment of my method and device is discussed in detail in connection with the accompanying drawing, which is for illustrative purposes only. This drawing includes the following figures (FIGS.), with like numerals indicating like parts.

DETAILED DESCRIPTION OF ONE ILLUSTRATIVE EMBODIMENT

FIGS. 1 through 3B illustrate one embodiment of my medical device used to practice my method of treating cancer generally indicated by the numeral 10.

The Device

Figure 1:
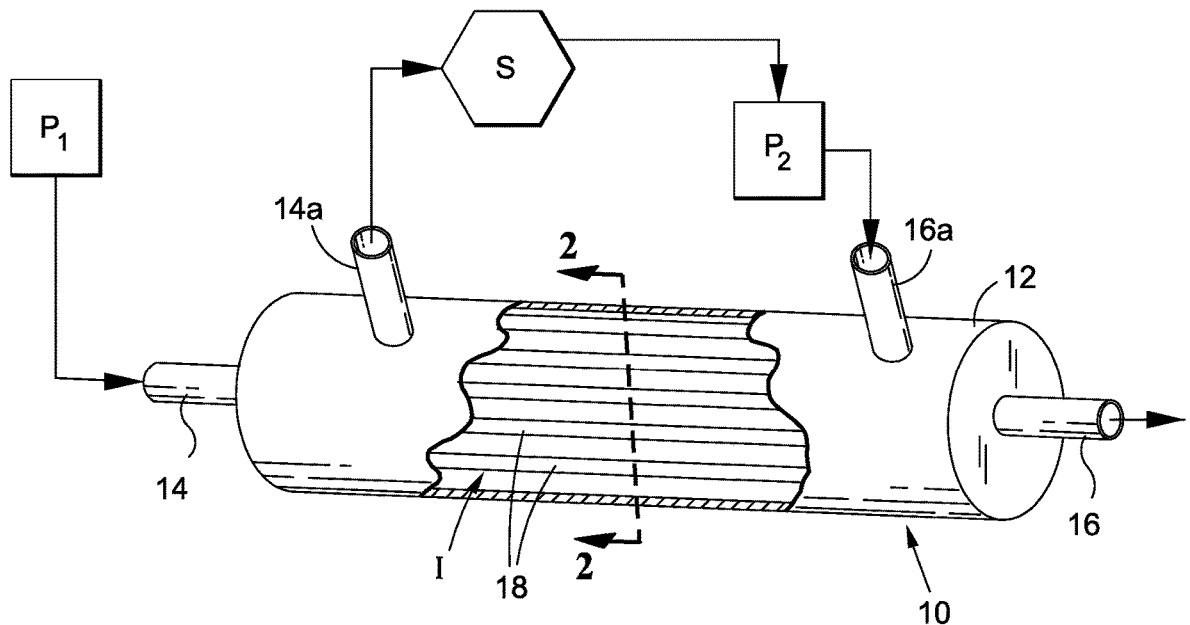
FIG. 1 is a perspective view of one embodiment of my device used in treating cancer according to my method.
Figure 2:
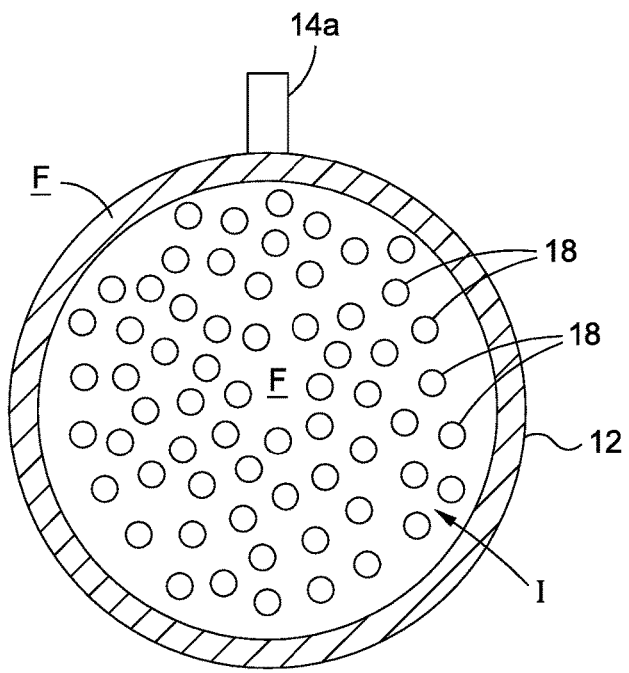
FIG. 2 is a cross-sectional view of taken along line 2-2 of FIG. 1.
Figure 3:
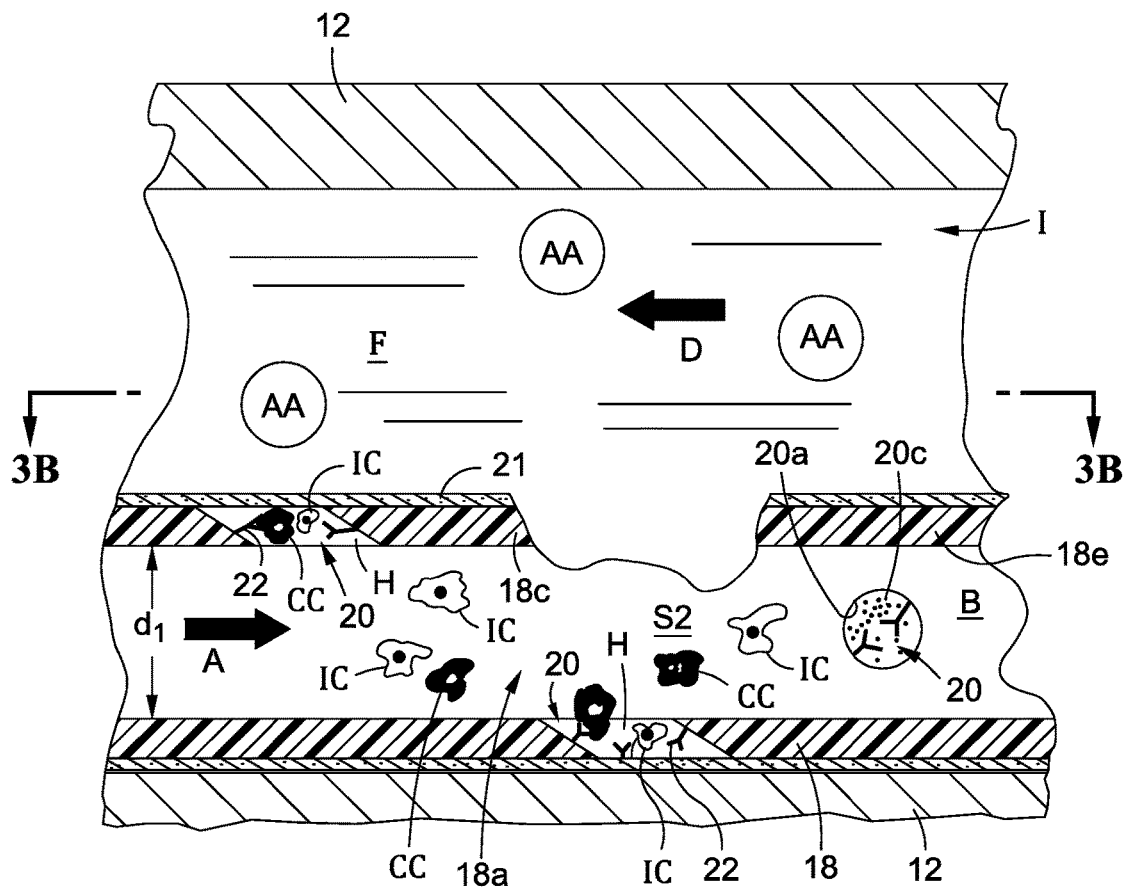
FIG. 3 is an enlarged fragmentary, cross-sectional view, with sections broken away, taken along line 3-3 of FIG. 3B, showing blood from a cancer patient flowing through a chamber of the device illustrated in FIG. 1.
Figures 3A, 3B:
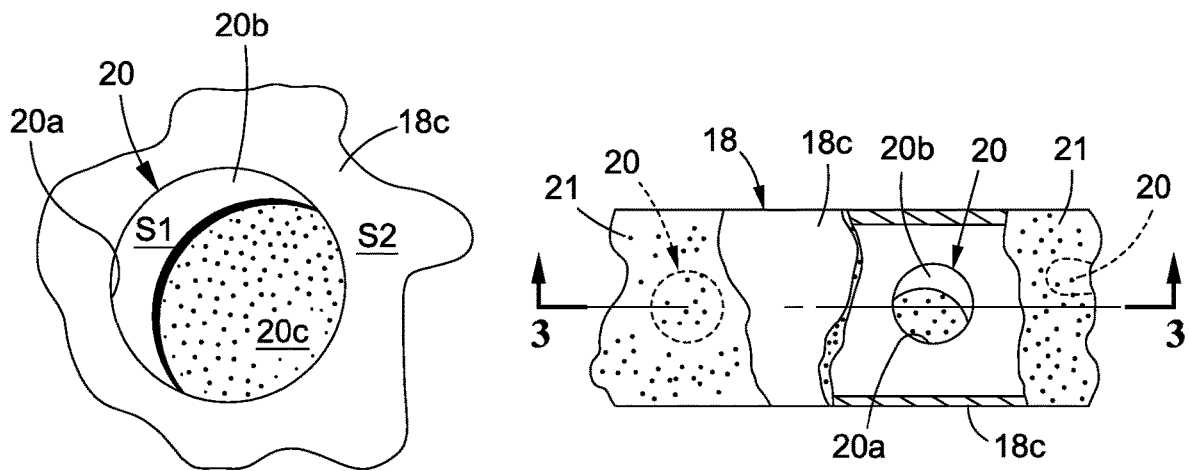
FIG. 3A is a fragmentary perspective view of a well in a tubular passageway of my device.
FIG. 3B is a cross-sectional view, with sections broken away, of taken along line 3B-3B of FIG. 3.

The medical device 10 comprises a hollow, cylindrical chamber 12 with an inlet 14 and an outlet 16 and a plurality of micro-tubes 18 within an interior I of the chamber. An individual micro-tube 18 forms within it a passageway 18a (FIG. 3) having an inside diameter $d_1$ substantially from 50 to 500 microns. An individual micro-tube 18 comprises a cylindrical tube 18c may be made of a plastic such as, for example, a polyvinyl chloride tube that is covered by a membrane film 21. A plurality of wells 20 are within internal surfaces S2 of the tubes 18c. The wells 20 may be formed by first creating numerous, small diameter holes H in the tubes 18c, for example, by using a laser beam. The beam may be at an angle so the holes H are offset with respect to each other. The edges of an individual hole H forms a slanted, non-porous, substantially cylindrical sidewall portion of an individual well 20. After perforation, the exterior surface of an individual tube 18c is covered with a membrane 21 that is bonded in position with an adhesive. The part of the membrane 21 that overlies a hole H forms a bottom wall 20c of an individual well 20 (FIG. 3A).

Open mouths 20a of the wells 20 are formed along the internal surface S2 of the tubes 18c of predetermined dimensions that enable immune cells and cancer cells in a patient's blood B flowing through the passageways 18a to pass through the open mouths and enter the wells. Typically, the mouth 20a of a well 20 has a diameter substantially from 20 to 200 microns and a depth substantially from 20 to 100 microns. The porous membrane 21 (FIG. 3A) has a predetermined pore size that enables an activating agent AA (chemotaxins and cytokines) introduced into a carrier fluid F in the interior I of the chamber 12 to pass through a well's porous membrane bottom wall 20c and enter the well yet prevents immune cells IC and cancer cells CC in the well to flow through the porous bottom wall into the interior of the chamber. Antibodies 22 are within the wells 20, for example, they may be attached well surfaces S1 (FIG. 3A).

The micro-tubes 18 are assembled within the interior I of the chamber 12 in a parallel array in fluid communication with a cancer patient through the inlet 14 and outlet 16 to circulate the patient's blood B through the passageways 18a. At the opposed ends of the array of micro-tubes 18 are manifolds (not shown) configured to direct blood into open entry ends of the micro-tubes 18 near the inlet 14, through the passageways 18a, and then out open exit ends of the micro-tubes near the outlet 16. A pump P1 may be used to so circulate the patient's blood B in a manner similar to dialysis, directing the blood to flow in the direction of the arrow A in FIG. 3. A pump P2 is used to pump a carrier fluid F containing an activating agent AA from a source S through a second inlet 14a in the chamber 12, through the interior I of the chamber, and then out a second outlet 16a in the chamber back to the source. As indicated by the arrow D, the pump P2 pumps the carrier fluid F in a direction of flow countercurrent to that of the blood B as it flows through the passageways 18a.

The Method

The device 10 is used to conduct my method of treating cancer. With the device 10 connected to the patient: The blood B from the cancer patient containing immune cells and cancer cells passes through the array of passageways 18a to enable the molecular-sized activating agent AA in the carrier fluid F to pass through the porous membrane bottom wall 20c and mingle with blood B in the wells 20. The controlled pore size of the pores of the bottom wall 20c prevent immune cells and cancer cells in the blood to pass through the membrane wall into the interior I of the chamber 12. Next the carrier fluid F containing the activating agent AA passes through the interior of the chamber 12 as the patient's blood B flows through the passageways 18a. This sequence, however, is not required and the carrier fluid F could be circulated through the interior of the chamber prior to introducing the blood B into the passageways. Regardless of the sequence, the patient's blood B is retained in the wells 20 for a predetermined period sufficient to enhance an immune response. The passage of molecules of the activating agent AA across the porous bottom wall 20c may be controlled by varying the pressure of the blood as the carrier fluid F and blood flow countercurrent relative to each other.

Advantageously, different activating agents AA may be periodically introduced into the carrier fluid F. For example, one of the different activating agents AA is a chemotaxin, for example, interleukine 8 (IL8), and the other different activating agent is a cytokine such as, for example, interleukine 2 (IL2). Circulating cancer cells CC floating in a patient's blood past the open mouth of a well 20 enter the well and are bound by the antibodies 22 to the well surface S1. For example, in a sequential fashion, chemotaxins are first introduced into the carrier fluid F and then cytokines such as lymphokines. The chemotaxin molecules form a concentration gradient within the wells 20 that entices immune cells IC into the wells 20 where cancer cells have been previously bound by the antibodies 22. By this process immune cells and cancer cells are directly juxtaposed, or at least placed in close proximity to one another. The lymphokines are next introduced into the carrier fluid F and circulated within the interior of the chamber 12 to permit the lymphokines to permeate through the porous membrane bottom wall 20c into the wells 20. Immune cell activation occurs specifically on the immune cells that are in close proximity to the circulating cancer cells.

After a suitable incubation period controlled by the rate of blood flow through the passageways 18a, the blood within the wells 20 now contains activated immune cells that are infused back into the patient as blood flows through the passageways. The cycle can then be repeated: blood flows into the wells 20 (delivering circulating cells to the wells), chemotaxin is flushed through the pores of the membrane bottom walls 20c (enticing immune cells IC into the wells), then a cytokine is flushed through the membrane bottom walls (activating the immune cells within the wells), then blood including the activated immune cells is delivered back to the patient. Circulating cancer cells CC bound within the device 10 are retained within the wells 20, should they survive.

My method may be carried out in a continuous flow fashion or a batch process. The dwell time of the cells being treated in the wells 20 is on average a minimum of 15 seconds, either by continuous or batch process. The connection to the patient may be intravenously or subcutaneously. My method of treating cancer cells CC in a patient's blood may be ex vivo and in line.

SCOPE OF THE INVENTION

The above presents a description of the best mode I contemplate of carrying out my method and of the manner and process of making and using my method and device, in such full, clear, concise, and exact terms as to enable a person skilled in the art to make and use. My method and device are, however, susceptible to modifications and alternate constructions from the illustrative embodiment discussed above which are fully equivalent. Consequently, it is not the intention to limit my method and device to the particular embodiment disclosed. On the contrary, my intention is to cover all modifications and alternate constructions coming within the spirit and scope of my method and device as generally expressed by the following claims, which particularly point out and distinctly claim the subject matter of my invention:

The invention claimed is:

1. A method of treating cancer comprising the steps of
   (a) positioning within an interior of a chamber an array of tubular passageways including porous membrane portions that enable a molecular-sized activating agent in a carrier fluid flowing through the chamber to pass through the porous membrane portions and enter a patient's blood flowing through the passageways, said porous membrane portions configured to prevent immune cells and cancer cells in said blood flowing through the passageways to pass through said porous membrane portions into the interior of the chamber, and (b) introducing the carrier fluid containing the molecular-sized activating agent into the interior of the chamber as the patient's blood flows through the passageways, different activating agents being periodically introduced into the carrier fluid, one of the different activating agents being a chemotaxin and the other different activating agent being a cytokine, and (c) retaining the patient's blood in the passageways to remain in contact with the immune cells and cancer cells in the patient's blood for a predetermined period sufficient to enhance an immune response.

2. The method of claim 1 where the flow of blood through the passageways is countercurrent to the flow of carrier fluid through the interior of the chamber.

* * * * *